(12) United States Patent
Bales

(10) Patent No.: US 6,508,820 B2
(45) Date of Patent: Jan. 21, 2003

(54) INTRAMEDULLARY INTERLOCK SCREW

(76) Inventor: Joel Patrick Bales, 77-760 Missouri Dr., Palm Desert, CA (US) 92211

(\*) Notice: Subject to any disclaimer, the term of this patent is extended or adjusted under 35 U.S.C. 154(b) by 0 days.

(21) Appl. No.: 09/776,264

(22) Filed: Feb. 2, 2001

(65) Prior Publication Data

US 2001/0034524 A1 Oct. 25, 2001

Related U.S. Application Data

(60) Provisional application No. 60/180,029, filed on Feb. 3, 2000.

(51) Int. Cl.$^7$ .............................................. A61B 17/58
(52) U.S. Cl. ............................ 606/73; 606/62; 606/64; 606/104
(58) Field of Search .............................. 606/64, 62, 63, 606/67, 68, 96, 98, 104, 72, 73, 75, 86; 411/310, 383, 302, 412, 413

(56) References Cited

U.S. PATENT DOCUMENTS

| | | | |
|---|---|---|---|
| 4,875,475 A | | 10/1989 | Comte et al. |
| 5,180,382 A | | 1/1993 | Frigg et al. |
| 5,242,447 A | * | 9/1993 | Borzone .................... 606/73 |
| 5,244,327 A | * | 9/1993 | Whitesell .................. 411/412 |
| 5,275,601 A | | 1/1994 | Gogolewski et al. |
| 5,340,254 A | * | 8/1994 | Hertel et al. ................ 411/310 |
| 5,573,548 A | * | 11/1996 | Nazre et al. ................ 606/73 |
| 5,584,836 A | | 12/1996 | Ballintyn et al. |
| 5,730,744 A | * | 3/1998 | Justin et al. ................. 606/73 |
| 5,935,127 A | * | 8/1999 | Border ....................... 606/62 |
| 6,019,761 A | * | 2/2000 | Gustilo ....................... 606/62 |
| 6,116,832 A | * | 9/2000 | Wolf et al. .................. 411/383 |
| 6,123,708 A | * | 9/2000 | Kilpela et al. ............... 606/62 |

\* cited by examiner

*Primary Examiner*—Pedro Philogene

(57) ABSTRACT

An intramedullary interlock screw includes an elongate shank having a preferably cylindrical shank outer surface, and an external thread disposed helically about the shank and having a thread outer surface coaxial with and substantially parallel to the shank outer surface. The shank diameter as determined by the shank outer surface is at least 0.75 times the thread diameter as determined by the thread outer surface, and most preferably is 0.85 - 0.9 times the thread diameter, resulting in a considerable reduction in thread height as compared to similarly sized conventional bone screws. Further, the thread outer surface has a width at least twenty percent of the thread pitch, a substantial increase over the corresponding percentage in conventional bone screws. Both features contribute to an increase in the strength of the screw, in terms of resistance to bending forces applied laterally, i.e. perpendicular to the screw length. The increased thread width in proportion to the thread pitch reduces undesirable stress concentrations at the interface of the interlock screw and an intramedullary nail secured by the interlock screw to a long bone, e.g. the tibia or femur. A bone fixation system typically employs an intramedullary nail in combination with several of the interlock screws, each screw adapted to extend laterally through an associated opening at one of the nail end regions.

35 Claims, 4 Drawing Sheets

INTRAMEDULLARY INTERLOCK SCREW

This application claims the benefit of priority based on U.S. Provisional Application No. 60/180,029 entitled Intramedullary Interlock Screw, filed Feb. 3, 2000.

BACKGROUND OF THE INVENTION

This invention relates to bone fracture fixation devices, and more particularly to systems that involve positioning of an intramedullary nail within the intramedullary canal, followed by cross-locking for fixation of the intramedullary nail to achieve bone fixation.

Intramedullary fixation is a well-accepted technique for internal fracture fixation of long bones, typically the femur or the tibia, although humeral and forearm (radial or ulnar) applications also are possible. This fixation technique involves inserting an intramedullary nail, usually a hollow shaft having a slight bend or curvature, into the intramedullary or marrow canal. Once inserted and properly positioned within the bone, the intramedullary nail is fixed to the bone by cross-locking, with screws extended transversely with respect to the elongated nail through the bone, and through holes in the intramedullary nail, or in the case of hollow nails, through diametrically opposed holes in the nail wall.

The cross-locking fixation technique is shown in U.S. Pat. No. 5,122,141 (Simpson, et al.), which also illustrates an inclined disposition of bone screws through the nail at the proximal end of the femur. U.S. Pat. No. 5,112,333 (Fixel) also illustrates an intramedullary nail secured in the femur using fasteners directed transversely of the nail.

FIG. 1 illustrates an intramedullary nail 1 within the intramedullary canal 2 of a long bone 3, for example the femur. The nail is fixed by two bone screws 4 and 5. Bone screw 4, extended through a wall 6 of the bone on opposite sides of the intramedullary nail, also extends through diametrically opposed holes 7 and 8 through the nail wall to secure the intramedullary nail within the intramedullary canal. Bone screw 5 extends in similar fashion through the bone wall and through openings 9 and 10 through the nail wall, to further secure the nail.

FIG. 2 is an enlarged view showing a portion of bone screw 4 extending through hole 7. The bone screw has an elongated shank 11 having a shank diameter constituting a "minor" diameter of the screw. An external thread 12 surrounds the shank, with the radial extremity of the thread determining a major diameter of the screw. The diameter of hole 7 closely approximates the major diameter of the bone screw, so that the thread extremity establishes a substantially helical contact or interface with the intramedullary nail along the wall defining hole 7.

Although this arrangement has in general been satisfactory, several difficulties arise due to the amplitude and direction of stresses at the intramedullary nail/screw interface. More particularly, both the tibia and the femur are required to support substantial body weight, and thus are subject to substantial axially directed compressive forces and substantial shock in the axial direction. The muscles also can exert twisting forces upon the bone. An intramedullary fixation system is subject to these same forces.

Fasteners such as bone screw 4 are designed primarily to bear loads in the axial direction with respect to the fastener, and thus are well suited for certain uses, e.g. securing bone plates. However, when used to interlock an intramedullary nail, the bone screw is subject to the aforementioned axial compressive stresses and twisting, which operate as sheer forces directed laterally or transversely with respect to the screw. In some cases, the sheer forces are of sufficient magnitude to fracture or break the bone screw at a point near the intramedullary nail hole that accommodates the screw.

One attempt to solve this problem involves using larger-diameter bone screws. A consequence of using larger screws is that the holes through the intramedullary nail needed to accommodate the screws must also be larger, which compromises the integrity of the nail. Accordingly, although larger screws may reduce the risk of screw failure due to sheer, they are likely to increase the risk of nail failure.

Another approach is to form the bone screws from a material selected for a high resistance to fracture, for example stainless steel. The materials selected to form the intramedullary nail and bone screws, however, must have a high degree of biocompatibility as well. Titanium and certain titanium-based alloys are highly preferred for their biocompatibility, despite their notch sensitivity characteristics as compared to stainless steel. Steel components lack the degree of biocompatibility desired in many applications. A "partial solution" of using a titanium intramedullary nail in combination with steel bone screws would not be satisfactory, due to galvanic corrosion at the nail/screw junctions.

Another approach addressing this problem is seen in U.S. Pat. No. 5,814,047 (Emilio, et al.). The Emilio patent describes a fixation system in which the intramedullary nail is secured by several flexible screws with distal end portions slightly inclined relative to the longitudinal nail extension, as opposed to more rigid, transverse screws. This arrangement, however, requires elongate flexible screws of different lengths, and structure within the nail for channeling these screws and diverting the tips at a slant relative to the nail.

Another problem caused by stresses laterally of the bone screws is a risk of plastic deformation of the screw threads, the interior of the holes through the nail wall accommodating the screws, or both as a result of the forces involved. For example with reference to FIGS. 2 and 3, as threads 12 and the internal surface of hole 7 are urged against one another, there is a high stress concentration along the thread/wall interface which can tend to flatten the external threads, or lead to depressions in the hole wall, or both, as indicated by the broken lines in FIG. 3. In any of these events the integrity of fixation is compromised. Any transverse loads can cause further plastic deformation, and may further compromise fixation.

Therefore, it is an object of the present invention to provide an interlock screw for securing an intramedullary nail, with an improved capacity to withstand forces directed laterally with respect to the screw, i.e. in directions perpendicular to the screw length.

Another object is to provide an intramedullary interlock screw with an external thread providing a larger area of contiguous surface contact at the interface with an intramedullary nail secured by the screw in a bone fixation application.

A further object is to provide a bone fixation system in which the components can be formed from a wider variety of materials, and yet maintain desired levels of strength and resistance to fatigue.

Yet another object is to provide an intramedullary interlock screw that has a reduced major diameter such that openings in intramedullary nails to accommodate the screws can be reduced in size, while maintaining in the screw a desired resistance to bending under laterally applied forces.

SUMMARY OF THE INVENTION

To achieve these and other objects, there is provided a fastener for securing a fixation member with respect to osseous material. The fastener includes an elongate shank formed of a biocompatible material and extended in an axial direction. The shank has a maximum shank diameter and a shank outer surface. An external thread, formed of a biocompatible material, is disposed helically about the shank. The external thread has a substantially uniform thread pitch in the axial direction and defines a thread outer surface substantially parallel to the shank outer surface and spaced apart from the shank outer surface by a thread height. The width of the thread outer surface in the axial direction is at least twenty percent of the thread pitch, and the maximum shank diameter is at least six times the thread height.

As compared to the previously known bone screw shown in FIGS. 1–3, the width of the thread outer surface, i.e. the crest length, is considerably larger in proportion to the pitch length. Also as compared to the known screw, the maximum shank diameter is at least six times the thread height, thus to provide a thread height or depth considerably less in proportion to the screw size than the height in the previously known bone screw.

Several advantages arise from the foregoing features. First, increasing the ratio of the shank diameter with respect to the radial depth or height of the threads, increases the shank size in proportion to the size of the screw. For a screw with a given major diameter, this increases the strength of the screw, particularly in terms of its capacity to resist bending in response to sheer forces, i.e. the forces typically directed longitudinally of the intramedullary nail and transversely of the interlock screw. In particular, because the resistance of the shank to bending increases in proportion to its diameter to the fourth power, a slight increase in shank diameter results in a considerable increase in strength.

The increase in crest length with respect to pitch increases the area of contiguous surface contact between the most radially outward surface of the threads, i.e. the crest, and the wall portion of the intramedullary nail forming the opening in which the screw resides. The compressive forces that drive the intramedullary nail against the screw are distributed over a larger surface area, reducing stress concentrations sufficiently to virtually eliminate plastic deformation of the threads or wall of the nail surrounding the threads. This maintains the integrity of the screw/nail coupling, for a more secure fixation of the intramedullary nail.

The increase in crest length in proportion to pitch also increases the strength of the interlock screw, because it increases the proportion of the overall screw length having the major (crest) diameter and diminishes the proportion having the minor (shank) diameter.

Another aspect of the present invention is an intramedullary interlock screw. The screw includes an elongate shank extended in an axial direction, and having a cylindrical shank outer surface defining a shank diameter. An external thread is disposed helically about the shank and has a thread outer surface substantially parallel to the shank outer surface. The thread outer surface is coaxial with the shank outer surface and defines a thread diameter. The external thread further has a thread pitch and a thread width in the axial direction. The thread width is at least twenty percent of the thread pitch.

More preferably, the thread width is about one-half of the thread pitch. Thus, the proportion of the screw length having the major (thread) diameter is increased and the proportion of the length having the minor (shank) diameter is reduced, enhancing the strength of the screw in terms of resisting bending in response to laterally applied forces.

According to another aspect of the present invention there is provided an interlock screw adapted to withstand lateral forces. The interlock screw includes an elongate shank having a shank axis and a cylindrical shank outer surface defining a shank diameter. An external thread is disposed helically about the shank and has a substantially uniform thread pitch in the axial direction. The thread is concentric on the shank and has a thread outer surface substantially parallel to the shank outer surface and spaced apart from the shank outer surface to define a thread diameter. The shank diameter is at least about 0.75 times the thread diameter.

Preferably the shank diameter is in the range of 0.8–0.9 times the thread diameter. More preferably, the shank diameter is at least 0.85 times the thread diameter.

Advantageously the external thread further has a thread width, in the axial direction, at least about 0.2 times the thread pitch.

The external thread can be formed with opposite side walls disposed between the shank outer surface and the thread outer surface. Preferably the side walls are inclined with respect to planes perpendicular to the shank axis. Further, junctions of the side walls with the shank outer surface are preferably rounded as opposed to forming sharp corners or edges. Junctions of the side walls with the thread outer surface likewise are preferably rounded. This tends to reduce stress concentrations, and is particularly advantageous when titanium or titanium-based alloys are used to form the interlock screw.

Yet another feature of the invention is a bone fixation system including an elongate intramedullary nail, at least one opening formed through the intramedullary nail at a first end region of the nail, at least one opening formed through the intramedullary nail at a second end region opposite the first end region, and a plurality of the interlock screws constructed according to the present invention, one such screw associated with each of the openings.

Thus in accordance with the present invention, intramedullary locking screws can be formed of materials selected for a high degree of biocompatibility, and with a desired level of resistance to laterally applied bending forces, without unduly enlarging the major (thread) diameters. The interlock screw further reduces the risk of plastic deformation of the screw threads and the portion of the intramedullary nail surrounding and contacting the screw threads. As a result, the screw-accommodating holes in intramedullary nails can be kept smaller, to better ensure the structural integrity of the nails.

IN THE DRAWINGS

For a further understanding of the above and other features and advantages, reference is made to the accompanying detailed description and to the drawings, in which.

DETAILED DESCRIPTION OF THE PREFERRED EMBODIMENTS

Figure 2:
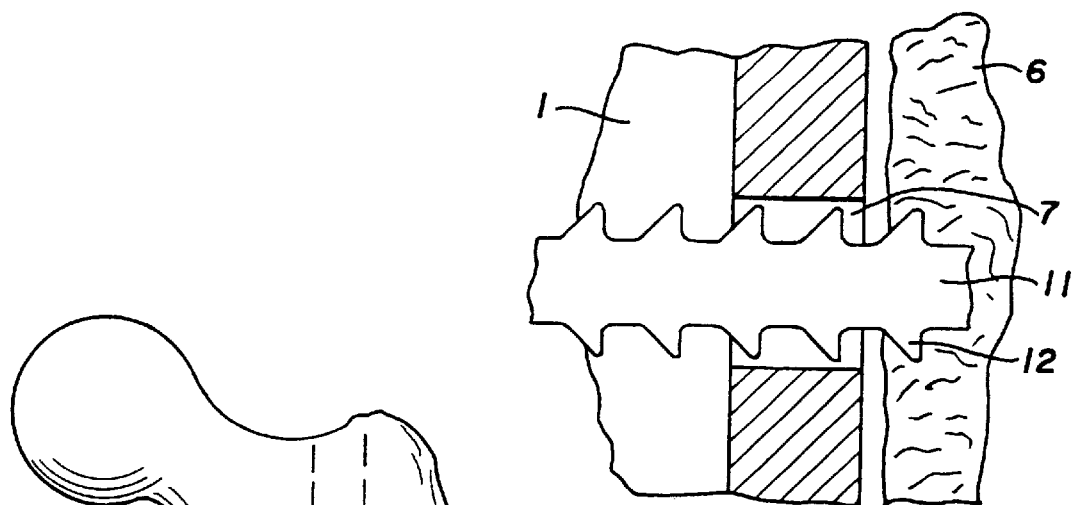
FIG. 2 is an enlarged suctioned view showing one of the bone screws of FIG. 1.
Figure 1:
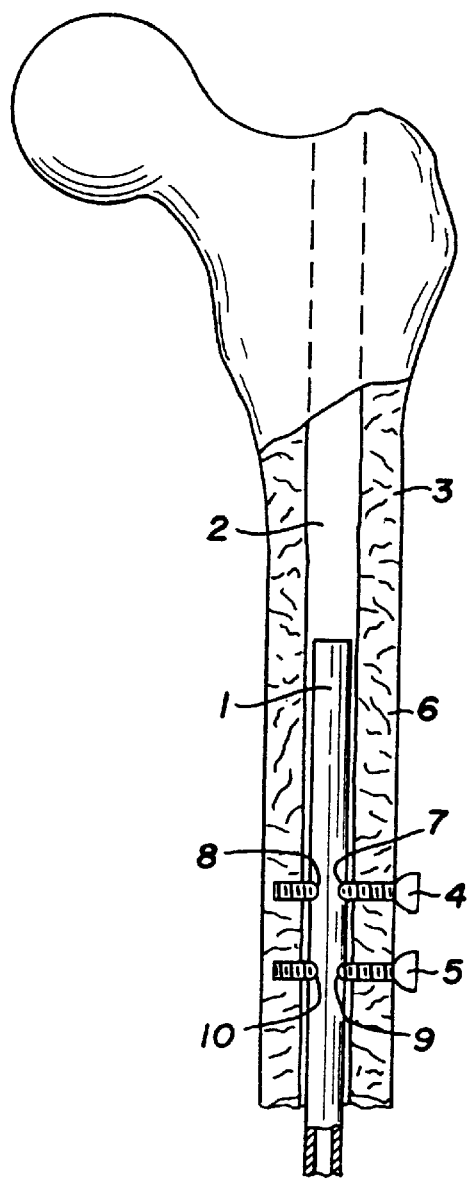
FIG. 1 is a partially sectioned view of a prior art intramedullary nail and bone screws fixing the nail within a femur.
Figure 3:
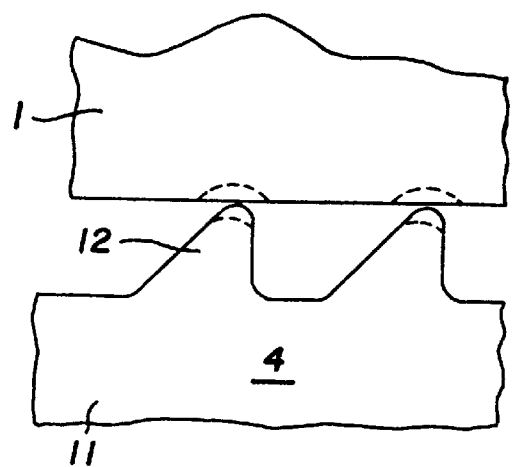
FIG. 3 is a further enlarged view schematically illustrating an interface of the bone screw with the intramedullary nail.
Figure 4:
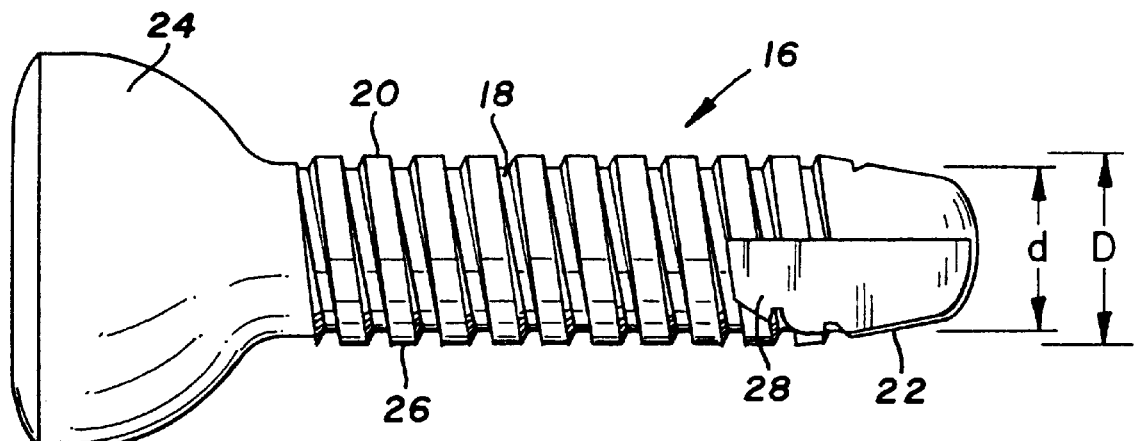
FIG. 4 is a side elevation of an intramedullary interlock screw constructed according to the present invention.

Returning to the drawings, there is shown in FIG. 4 an intramedullary interlock screw 16 constructed according to the present invention. Screw 16 includes an elongate shank 18, a helical external thread 20 disposed about the shank, a tapered tip 22 at one end, and a head 24 at the other end. Shank 18 has a diameter "d," which can be thought of as a minor diameter of interlock screw 16. Thread 20, more particularly a crest 26 or radially outward surface of the thread, defines a major diameter "D" of the interlock screw.

Figure 5:
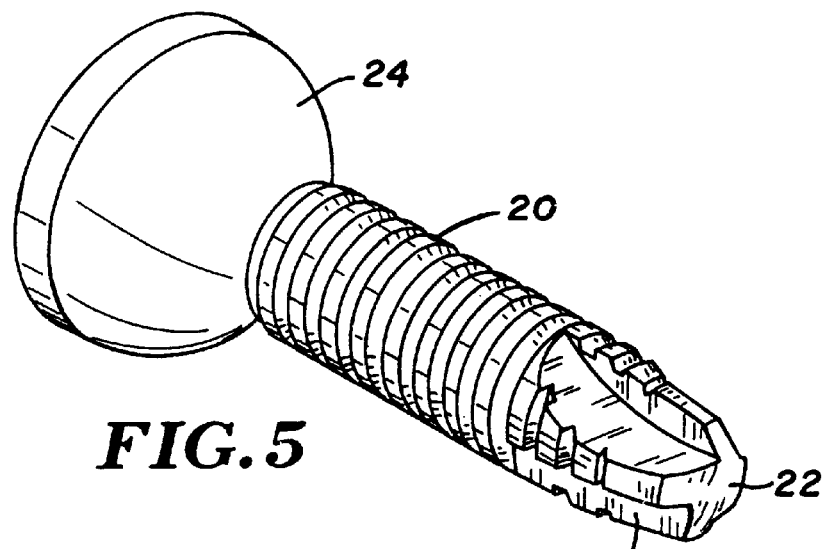
FIG. 5 is a perspective view of the interlock screw shown in FIG. 4.
Figure 6:
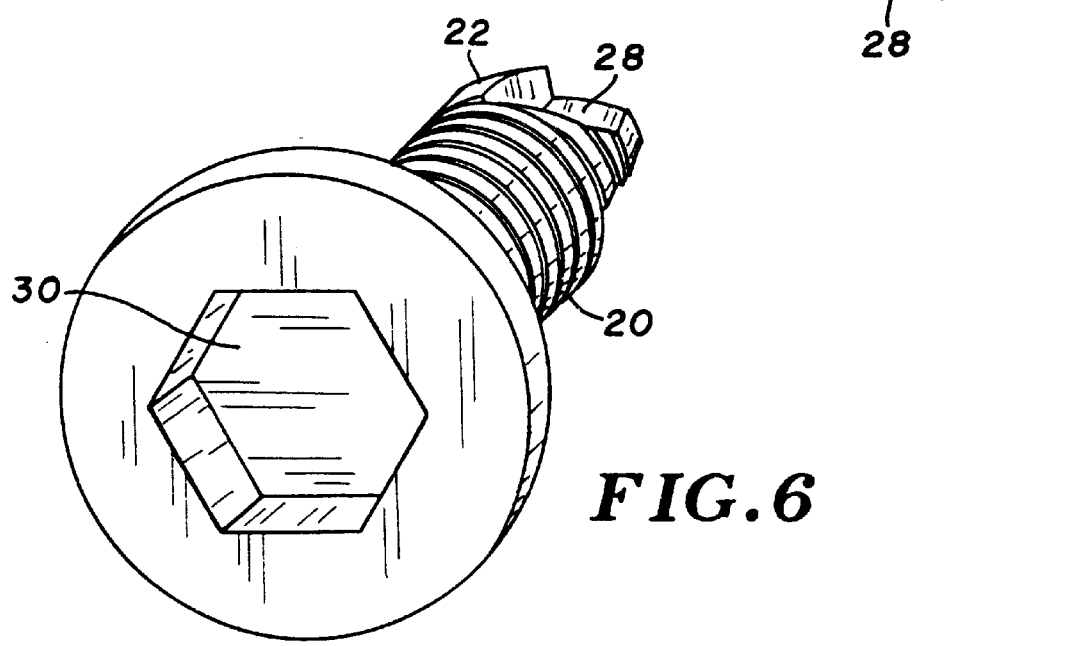
FIG. 6 is another perspective view of the interlock screw.

Tip 22 includes four cut-outs 28, each cut-out having a curvature as perhaps best seen in the perspective view of FIG. 5. The cut-outs enhance a self-tapping capability of screw 16 when entering osseous material. As seen in FIG. 6, also a perspective view, a hexagonal recess 30 is formed into head 24. Recess 30 is adapted to receive a similarly sized and shaped shaft of a drive tool (not shown) used to turn the interlock screw when installing the screw into the bone to effect a fixation of the intramedullary nail.

Figure 7:
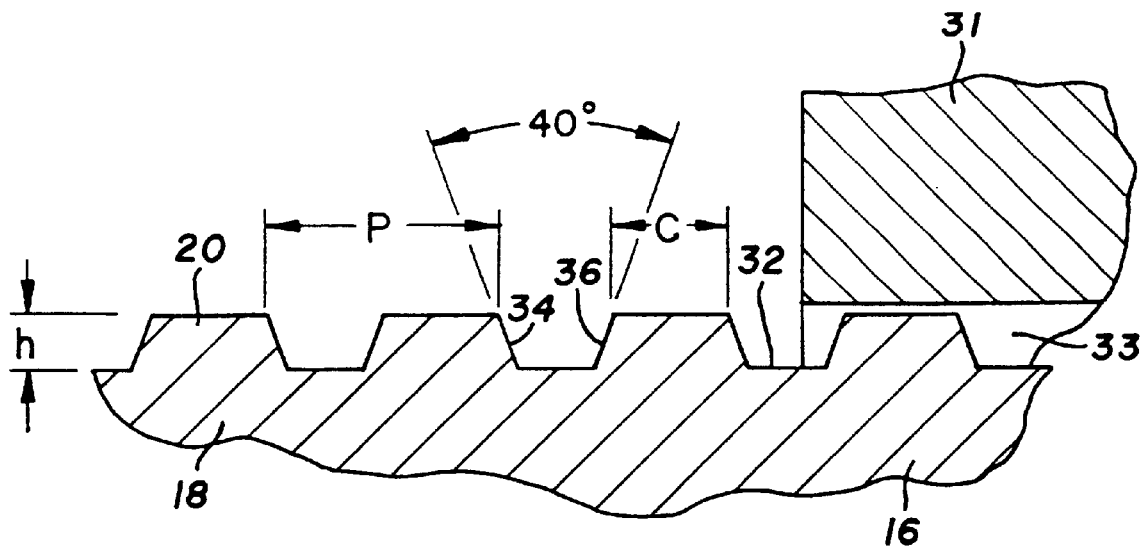
FIG. 7 is an enlarged sectioned view showing a portion of the interlock screw and part of an intramedullary nail interfacing the screw.

In FIG. 7, an enlarged portion of shank 18 and thread 20 is shown in section, to illustrate the thread profile. An intramedullary nail wall and hole are indicated at 31 and 33, respectively. The thread includes radially outward surface or crest 26 that appears flat in FIG. 7, but actually defines a circular cylinder as perhaps best seen from FIGS. 5 and 6. A root 32, i.e. the outer surface of the shank, also defines a circular cylinder, spaced radially inward from crest 26 by a height or depth shown as "h." The circular cylinders defined by the crest and the root have the major and minor diameters, respectively. The root and crest are joined by flanks 34 and 36, each inclined 20 degrees from the vertical as seen in FIG. 7 to define an angle of 40 degrees between opposing flanks. The axial distance between successive turns of thread 20, the pitch, is indicated at "P." The axial length of the crest is indicated at "C."

According to one specific embodiment of the intramedullary interlock screw, the thread pitch "P" is one millimeter (0.04 inches), and the crest length "C" is 0.5 mm (0.02 inches). The thread height "h" is 0.25 mm (0.01 inches). The axial dimension of the root is about 0.32 mm. The shank (minor) diameter is 3.25 mm (0.130 inches), and the crest (major) diameter is 3.75 mm (0.150 inches). Interlock screws according to this embodiment have lengths ranging from 26 mm (1.21 inches) to 65 mm (2.74 inches). Suitable materials for the screws include titanium, titanium alloys, and certain stainless steels.

According to another specific embodiment, the interlock screw has a shank diameter of 4.25 mm (0.169 inches) and a crest cylinder diameter of 4.75 mm (0.189 inches). Accordingly, the thread height "h" is the same as in the previous embodiment. The thread pitch and crest length also are the same. Lengths range from 26 mm to 75 mm (3.13 inches).

In the first specific embodiment the ratio of minor diameter/major diameter is about 0.87; while in the second embodiment this ratio is approximately 0.90. In both embodiments, the crest axial dimension is one-half of the thread pitch.

As noted above, the minor diameter, i.e. the diameter of shank 18, is at least seventy-five percent of the major diameter, i.e. the diameter determined by crest 26. The major diameter D exceeds the minor diameter d by twice the height h. Accordingly, with reference to the minor diameter and height, the minor diameter d is at least six times the height h. More preferably, minor diameter d is in the range of 8–18 h, and more preferably yet the diameter is at least about 11 times the thread height.

Figure 8:
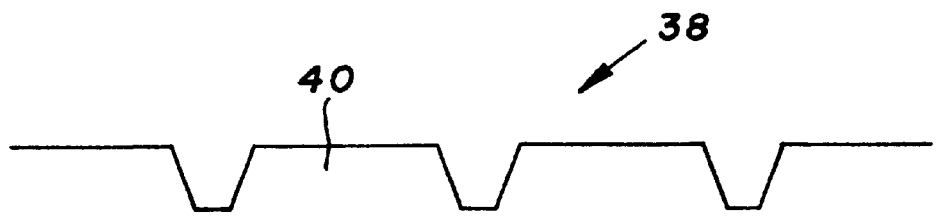
FIG. 8 is a schematic view showing the thread of an alternative embodiment intramedullary interlock screw.

FIG. 8 illustrates the thread profile of an alternative embodiment intramedullary interlock screw 38, in which the axial pitch is 0.8 mm, the crest axial dimension is 0.5 mm as before, and the axial root dimension is reduced to about 0.1 mm. Thus, the crest length is about sixty-three percent of the pitch. As compared to interlock screw 16, screw/nail contact forces are distributed over a larger contact area. Also, assuming the same major and minor diameters, interlock screw 38 exhibits increased resistance to bending under shear stress, because a greater proportion of the screw length has the major diameter. However, the reduced gap between adjacent turns of the thread 40 may diminish the self-anchoring capability of interlock screw 38.

Figure 9:
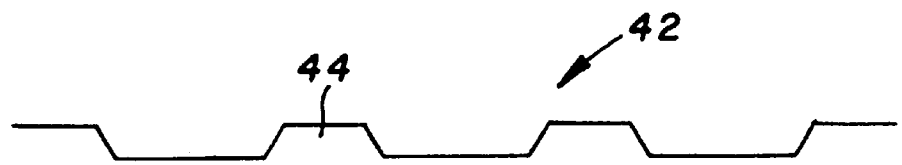
FIG. 9 is a schematic view showing the thread of another alternative embodiment interlock screw.

FIG. 9 illustrates the thread profile of another alternative embodiment interlock screw 42, in which the pitch is 1 mm. However, the crest axial length is reduced to 0.2 mm and the root axial dimension is about 6 mm. In view of the increased axial spacing between adjacent turns of thread 44, the thread height "h" is reduced by about one-half, to 0.12 mm. Accordingly, interlock screw 42, assuming it has the same major diameter as interlock screw 16, is stronger due to the larger minor diameter. However, stresses at the screw/nail interface are distributed over a smaller surface contact area, and thus are more concentrated.

Figure 10:
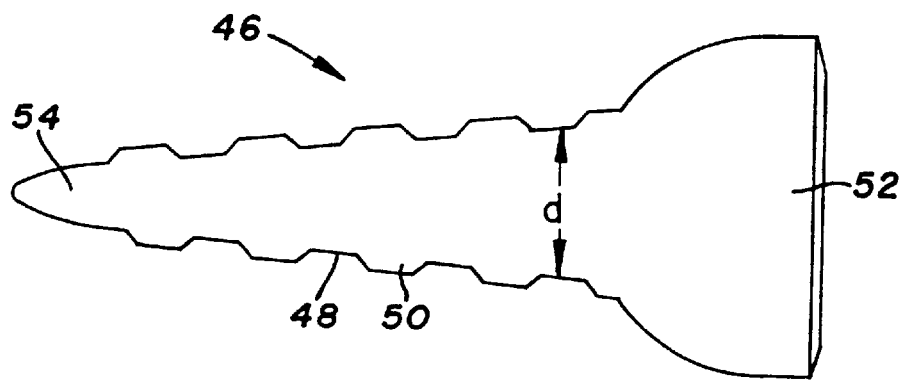
FIG. 10 is a schematic view showing the profile of a conical intramedullary interlock screw.

FIG. 10 is a schematic view showing an intramedullary interlock screw 46 with a conical shank 48 and an external thread 50 wound helically about the conical shank. A head 52 is disposed at a proximal end of the shank, and a tapered tip 54 extends from the shank distal end. A maximum diameter d of the shank, near the proximal end, preferably is at least six times the height of the external thread.

Figure 11:
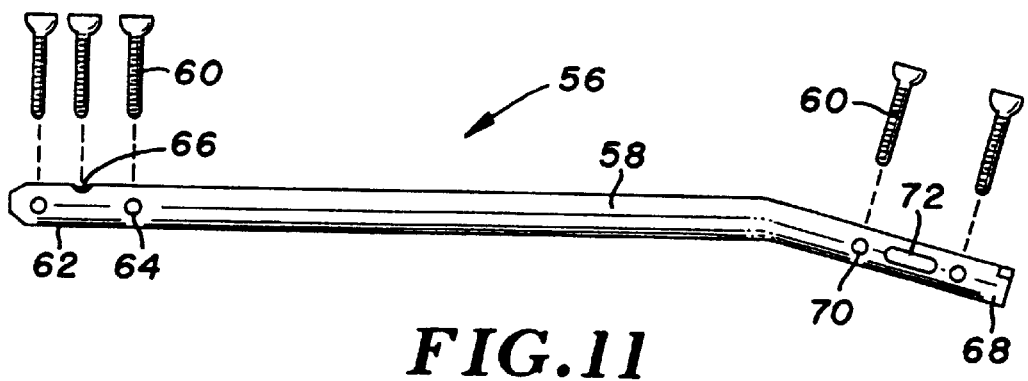
FIG. 11 illustrates a bone fixation system according to the present invention for use in tibial applications.

FIG. 11 illustrates a bone fixation system 56 including an intramedullary nail 58 suited for tibial applications, and a plurality of interlock screws 60, which can be similar to screws 16 or any of the foregoing cylindrical shank embodiments. A plurality of openings are formed through intramedullary nail 58 at its distal end 62, particularly two openings 64 for securing interlock screws in a lateral plane, and an opening 66 for securing another screw in an anterior/posterior plane. At the proximal end 68 of nail 58, two circular openings 70 and one elongate opening 72 extend through the nail.

Figure 12:
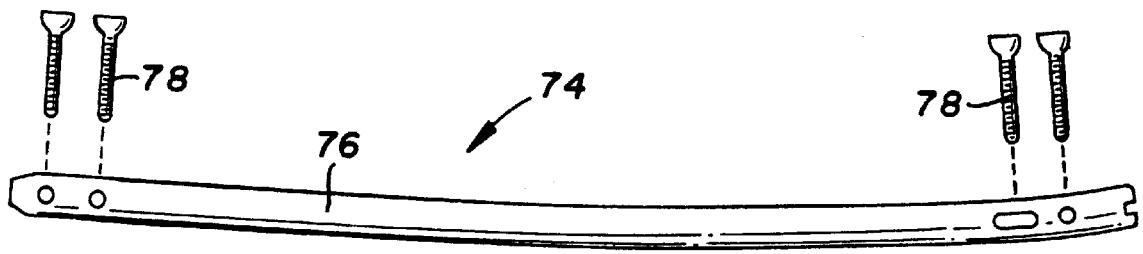
FIG. 12 illustrates a bone fixation system according to the present invention for use in femural applications.

FIG. 12 illustrates a bone fixation system 74 according to the present invention, including an intramedullary nail 76 suited for femural applications, along with a plurality of interlock screws 78 constructed according to a chosen one of the preceding embodiments.

Regardless of which of the foregoing embodiments is employed, substantial advantages are achieved in intramedullary fixation systems employing the intramedullary interlock screw in lieu of the conventional bone screw. The interlock screw, because of its greater proportionate crest length and smaller thread depth, affords considerably enhanced resistance to shear and resistance to fatigue, to afford a more secure and reliable fixation of the intramedullary nail.

What is claimed is:

1. A fastener for securing a fixation member with respect to osseous material, comprising:
   an elongate shank formed of a biocompatible material and extended in an axial direction, the shank having a maximum shank diameter and a shank outer surface;
   an external thread formed of a biocompatible material and disposed helically about the shank, the external thread having a substantially uniform thread pitch in the axial direction and defining a thread outer surface substantially parallel to the shank outer surface and spaced apart from the shank outer surface by a thread height; and
   the thread outer surface is of a width in the axial direction that is at least twenty percent of the thread pitch, and the maximum shank diameter is at least six times the thread height.

2. The fastener of claim 1 wherein:
   the width of the thread outer surface is about one-half the thread pitch.

3. The fastener of claim 1 wherein:
   the shank maximum diameter is about 8–18 times the thread height.

4. The fastener of claim 3 wherein:
   the thread width is at least about 11 times the thread height.

5. The fastener of claim 1 wherein:
   the shank outer surface and the thread outer surface are cylindrical whereby the shank has the maximum shank diameter substantially over its entire axial length, and the thread outer surface defines a substantially uniform thread diameter.

6. The fastener of claim 5 wherein:
   the maximum shank diameter is at least about 0.8 times the thread diameter and at most about 0.9 times the thread diameter.

7. The fastener of claim 5 wherein:
   the external thread includes opposite side walls disposed between the shank outer surface and the thread outer surface, and the side walls are at least slightly inclined with respect to planes taken normal to the axial direction.

8. The fastener of claim 7 wherein:
   the junctions of the side walls with the shank outer surface, and of the side walls with the thread outer surface, are rounded.

9. The fastener of claim 1 further including:
   a head disposed at one end of the shank and incorporating a feature coaxial with the shank and having a non-circular profile adapted to accommodate a tool shaped to correspond to said profile and operable to rotate the shank about an axis thereof.

10. The fastener of claim 9 wherein:
    the head has a head diameter larger than the thread diameter, and the feature comprises a hexagonal recess formed in the head.

11. The fastener of claim 10 further including:
    a tapered tip disposed at an end of the shank opposite from the head.

12. The fastener of claim 1 wherein:
    the shank is conical, whereby the shank outer surface and the thread outer surface are tapered.

13. The fastener of claim 12 further including:
    a head disposed at a larger end of the shank and having a head diameter larger than the maximum shank diameter, and a tapered tip at a narrower end of the shank extended beyond the external thread.

14. A bone fixation system comprising:
    an elongate intramedullary nail, at least one first opening formed through the intramedullary nail at a first end region thereof, and at least one second opening formed through the intramedullary nail at a second end region thereof, opposite the first region; and
    a plurality of fasteners, each of said fasteners comprising:
      an elongate shank formed of a biocompatible material and extended in an axial direction, the shank having a maximum shank diameter and a shank outer surface;
      an external thread formed of a biocompatible material and disposed helically about the shank, the external thread having a substantially uniform thread pitch in the axial direction and defining a thread outer surface substantially parallel to the shank outer surface and spaced apart from the shank outer surface by a thread height; and
      the thread outer surface is of a width in the axial direction that is at least twenty percent of the thread pitch, and the maximum shank diameter is at least six times the thread height; and
    one of the fasteners is associated with each of the openings through the intramedullary nail.

15. An intramedullary interlock screw comprising:
    an elongate shank formed of a biocompatible material and extended in an axial direction, having a cylindrical shank outer surface defining a shank diameter; and
    an external thread disposed helically about the shank and having a thread outer surface substantially parallel to the shank outer surface, coaxial with the shank outer surface, and defining a thread diameter, the external thread further having a thread pitch and a thread width in the axial direction, and the thread width is at least twenty percent of the thread pitch.

16. The interlock screw of claim 15 wherein:
    the thread width is about one-half the thread pitch.

17. The interlock screw of claim 15 wherein:
    the shank diameter is at least about 0.75 times the thread diameter.

18. The interlock screw of claim 17 wherein:
    the shank diameter is in the range of 0.8–0.9 times the thread diameter.

19. The interlock screw of claim 15 wherein:
    the external thread further includes opposite side walls disposed between the outer shank surface and the outer thread surface, the side walls being inclined with respect to planes taken transversely of the shank.

20. The interlock screw of claim 19 wherein:
    junctions of the side walls with the shank outer surface, and of the side walls with the thread outer surface, are rounded.

21. The interlock screw of claim 15 further including:
    a head disposed at one end of the shank and incorporating a feature coaxial with the shank and defining a non-circular profile in transverse planes, thereby to accommodate a tool shaped to correspond to said profile and operable to rotate the shank about an axis thereof.

22. The interlock screw of claim 21 wherein:

the head has a head diameter larger than the thread diameter, and said structure comprises a hexagonal recess formed in the head.

23. The interlock screw of claim 22 further including:

a tapered tip disposed at an end of the shank opposite from the head.

24. A bone fixation system comprising:

an intramedullary nail, at least one first opening formed through the intramedullary nail at a first end region thereof, and at least one second opening formed through the intramedullary nail at a second and opposite end region thereof, and a plurality of the interlock screws, each of the screws comprising:

an elongate shank formed of a biocompatible material and extended in an axial direction, having a cylindrical shank outer surface defining a shank diameter; and an external thread disposed helically about the shank and having a thread outer surface substantially parallel to the shank outer surface, coaxial with the shank outer surface, and defining a thread diameter, the external thread further having a thread pitch and a thread width in the axial direction, and the thread width is at least twenty percent of the thread pitch; and one of the interlock screws is associated with each one of the first and second openings.

25. An interlock screw adapted to withstand lateral forces, comprising:

an elongate shank having a shank axis and a cylindrical shank outer surface defining a shank diameter;

an external thread disposed helically about the shank and having a substantially uniform thread pitch in the axial direction, the thread being concentric on the shank and having a thread outer surface substantially parallel to the shank outer surface and spaced apart from the shank outer surface to define a thread diameter; and the shank is of a diameter at least about 0.75 times the thread diameter.

26. The interlock screw of claim 25 wherein:

the shank diameter is in the range of 0.8–0.9 times the thread diameter.

27. The interlock screw of claim 26 wherein:

the shank diameter is at least 0.85 times the thread diameter.

28. The interlock screw of claim 25 wherein:

the external thread further has a thread width in the axial direction, and the thread width is at least about 0.2 times the thread pitch.

29. The interlock screw of claim 28 wherein:

the thread width is about one-half the thread pitch.

30. The interlock screw of claim 25 wherein:

the external thread further includes opposite side walls disposed between the shank outer surface and the thread outer surface, wherein the side walls are inclined with respect to planes perpendicular to the shank axis.

31. The interlock screw of claim 30 wherein:

junctions of the side walls with the shank outer surface, and of the side walls with the thread outer surface, are rounded.

32. The interlock screw of claim 25 further including:

a head disposed at one end of the shank and incorporating a non-circular feature concentric with the shank and adapted for an engagement with a non-circular tool used to rotate the shank about the axis.

33. The interlock screw of claim 32 wherein:

the head has a head diameter larger than the thread diameter, and the non-circular feature comprises a hexagonal recess formed in the head.

34. The interlock screw of claim 33 further including:

a tapered tip disposed at a second and opposite end of the shank.

35. A bone fixation system comprising:

an elongate intramedullary nail, at least one first opening formed through the intramedullary nail at a first end region thereof, and at least one second opening formed through the intramedullary nail at a second end region opposite the first end region; and a plurality of the interlock screws, each of the screws comprising:

an elongate shank having a shank axis and a cylindrical shank outer surface defining a shank diameter;

an external thread disposed helically about the shank and having a substantially uniform thread pitch in the axial direction, the thread being concentric on the shank and having a thread outer surface substantially parallel to the shank outer surface and spaced apart from the shank outer surface to define a thread diameter; and the shank is of a diameter at least about 0.75 times the thread diameter; and one of the screws is associated with each one of the first and second openings.

\* \* \* \* \*